(12) United States Patent
Gouda et al.

(10) Patent No.: US 9,970,847 B2
(45) Date of Patent: May 15, 2018

(54) METHOD FOR STAINING TISSUE

(71) Applicants: Konica Minolta, Inc., Tokyo (JP); Tohoku University, Sendai-shi, Miyagi (JP)

(72) Inventors: Hideki Gouda, Tokyo (JP); Hideki Hoshino, Kokubunji (JP); Kensaku Takanashi, Hachioji (JP); Yasushi Nakano, Hino (JP); Kohsuke Gonda, Sendai (JP); Noriaki Ohuchi, Sendai (JP); Mika Watanabe, Sendai (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days. days.

(21) Appl. No.: 14/387,730

(22) PCT Filed: Mar. 26, 2013

(86) PCT No.: PCT/JP2013/058701
§ 371 (c)(1),
(2) Date: Sep. 24, 2014

(87) PCT Pub. No.: WO2013/146741
PCT Pub. Date: Oct. 3, 2013

(65) Prior Publication Data
US 2015/0064717 A1    Mar. 5, 2015

(30) Foreign Application Priority Data

Mar. 30, 2012 (JP) .................................. 2012-080782

(51) Int. Cl.
*G01N 1/30* (2006.01)
*G01N 21/64* (2006.01)
*G01N 33/50* (2006.01)
*G01N 33/535* (2006.01)
*G01N 33/58* (2006.01)
*G01N 33/552* (2006.01)
*G01N 33/52* (2006.01)
*G01N 33/569* (2006.01)

(52) U.S. Cl.
CPC ........... *G01N 1/30* (2013.01); *G01N 21/6428* (2013.01); *G01N 33/5082* (2013.01); *G01N 33/52* (2013.01); *G01N 33/535* (2013.01); *G01N 33/552* (2013.01); *G01N 33/56966* (2013.01); *G01N 33/581* (2013.01); *G01N 33/582* (2013.01)

(58) Field of Classification Search
CPC .. G01N 1/30; G01N 21/6428; G01N 33/5082; G01N 33/52; G01N 33/535; G01N 33/552; G01N 33/56966; G01N 33/581; G01N 33/582
See application file for complete search history.

(56) References Cited

U.S. PATENT DOCUMENTS

| 6,642,062 B2 * | 11/2003 | Kauvar ............ G01N 33/54313 435/6.1 |
| 2003/0148544 A1 * | 8/2003 | Nie et al. ........................ 436/524 |
| 2003/0231791 A1 * | 12/2003 | Torre-Bueno ...... G01N 21/6428 382/133 |
| 2008/0212172 A1 * | 9/2008 | Zhu .................... G01N 21/6458 359/383 |
| 2008/0299555 A1 | 12/2008 | Nitta et al. |
| 2013/0157287 A1 | 6/2013 | Takanashi et al. |

FOREIGN PATENT DOCUMENTS

| JP | 2008-298654 | 12/2008 | |
| WO | WO 2009117139 A2 * | 9/2009 | ........... G01N 33/533 |
| WO | 2012/029752 | 3/2012 | |

OTHER PUBLICATIONS

Bakalova et al., Quantum Dot-Based Western Blot Technology for Ultrasensitive Detection of Tracer Proteins, J. Am. Chem. Soc. 2005, 127, 9328-9329.*
Bratthauer, The Avidin-Biotin Complex (ABC) Method and Other Avidin-Biotin Binding Methods, Immunocytochemical Methods and Protocols vol. 115 of the series Methods in Molecular Biology™ pp. 203-214, 1999.*
International Search Report, PCT/JP2013/05871, in Japanese and English (total 5 pages), dated May 14, 2013.
International Report and Written Opinion in Japanese and English (8 pages), dated May 14, 2013.
Article by David L. Rimm, What brown cannot do for you, vol. 24, No. 8, Aug. 2006. Nature Biotechnology, pp. 914-916.
Article by Emma Barrow. A comparative study of quantitative immunohistochemistry and qunatum dot immunohistochemistry for mutation carrier identification in Lynch syndrome. J. Clin. Pathol 2011; 64: pp. 208-214.
The Extended European Search Report dated Aug. 7, 2015, issued from the corresponding European Application No. 13768930.3.
Ridvan Say, et al "Bioconjugated and Cross-Linked Bionanostructures for Bifunctional Immunohistochemical Labeling" Microscopy and Microanalysis, Springer, New York, NY, US, vol. 18, No. 2, Mar. 13, 2012, pp. 324-330.
Takaya Murakami, et al. "A novel method for detecting HIV-1 by non-radioactive in situ hybridization: Application of a peptide nucleic acid probe and catalysed signal amplification" The Journal of Pathology, vol. 194, No. 1, Jan. 1, 2001 pp. 130-135.
Berghorn K, et al. "cFos Immunoreactivity Is Enhanced with Biotin Amplification" Journal of Histochemistry and Cytochemistry, Histochemical Society, New York, NY, US, vol. 42, No. 12, Dec. 1, 1994, pp. 1635-1642.
Harris N. "Localisation of mRNA for Pea Legumin: in situ hybridization using a biotinylated cDNA probe", Protoplasma, vol. 130, Jan. 1, 1986, pp. 57-67.

(Continued)

*Primary Examiner* — Andrea S Grossman
(74) *Attorney, Agent, or Firm* — Lucas & Mercanti, LLP

(57) ABSTRACT

Provided is a method for staining a tissue enabling highly precise staining, by which the expression amount and/or the location of a biological substance in a tissue sample can be detected with a high quantitativity together with detailed information that can be obtained by bright field observation. The tissue staining method of the present invention is a method for staining a tissue, in which both staining that allows bright field observation and fluorescence staining are carried out for the same specific biological substance.

6 Claims, 4 Drawing Sheets

(56) References Cited

OTHER PUBLICATIONS

Official Notification of Reasons for Refusal dated Oct. 25, 2016 from corresponding Japanese Application No. JP 2014-507895; English translation of Official Notification of Reasons for Refusal; Total of 7 pages.
European Office Action, 13768930.3, dated Nov. 27, 2017.

\* cited by examiner

[Fig. 1]
Mode 1s
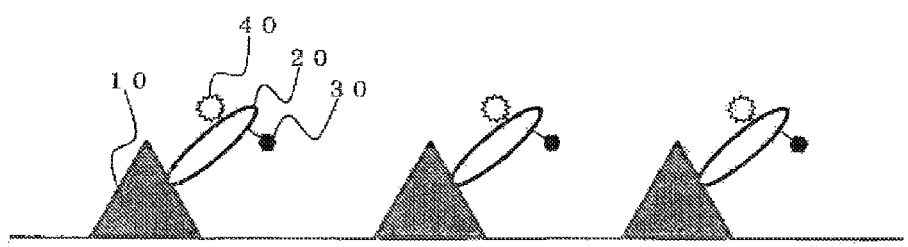
Mode 2
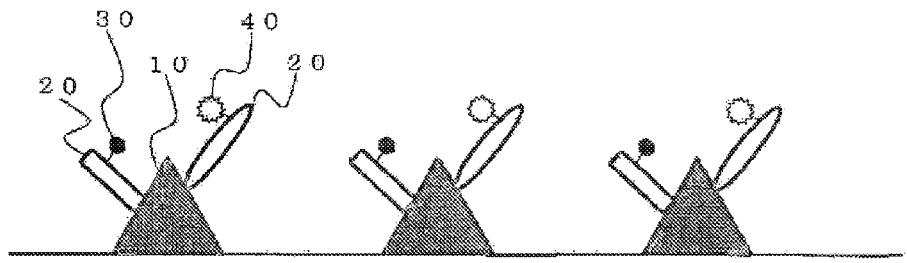

[Fig. 2]
Mode 1A
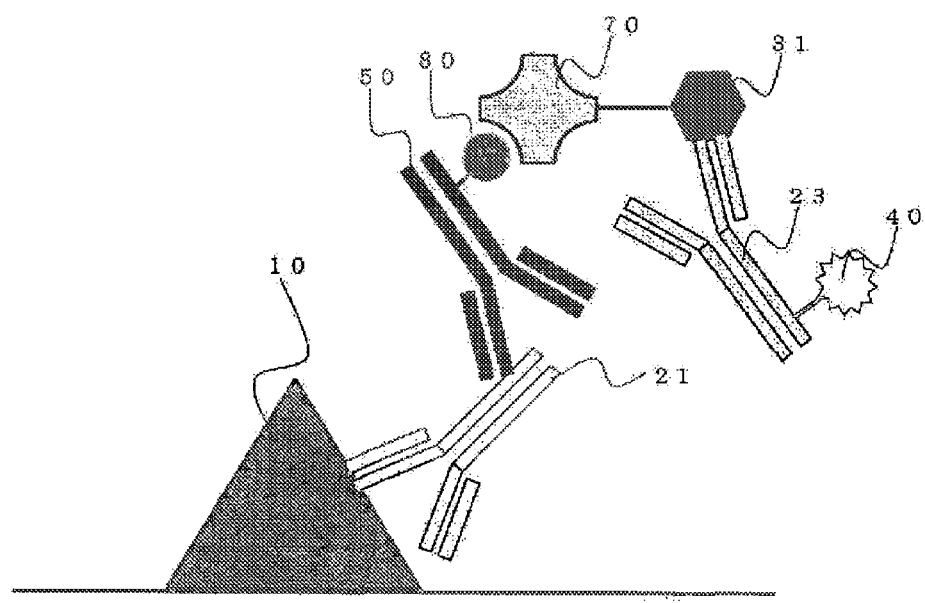

[Fig. 3]
Mode 1B
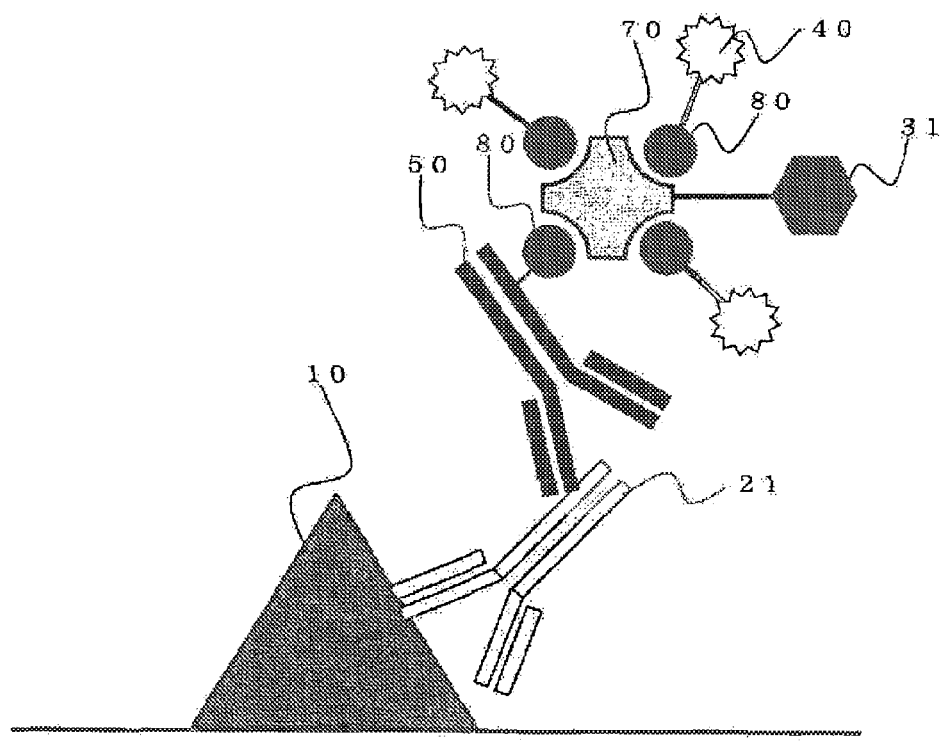

[Fig. 4]
DBA Staining (Upper) and Fluorescence Staining (Lower) in Same Visual Field
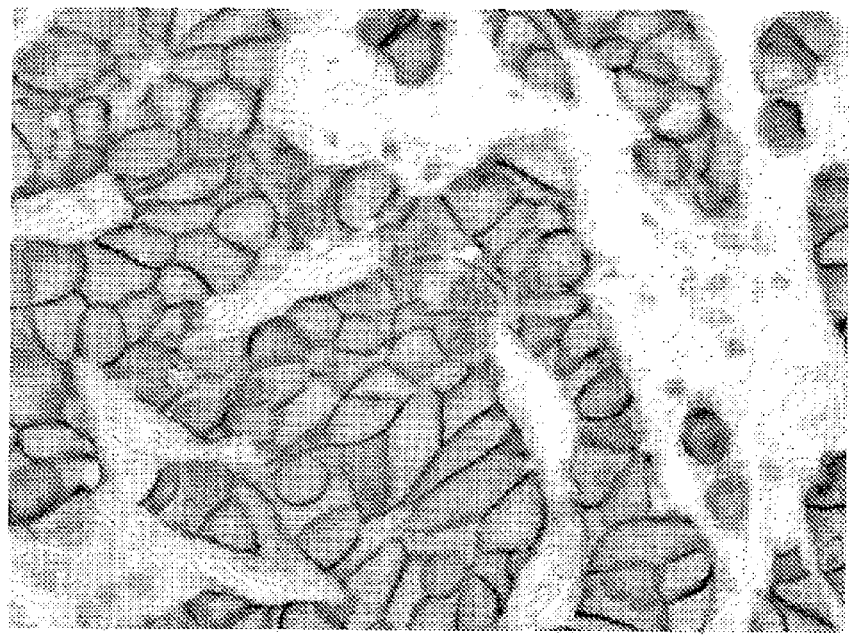
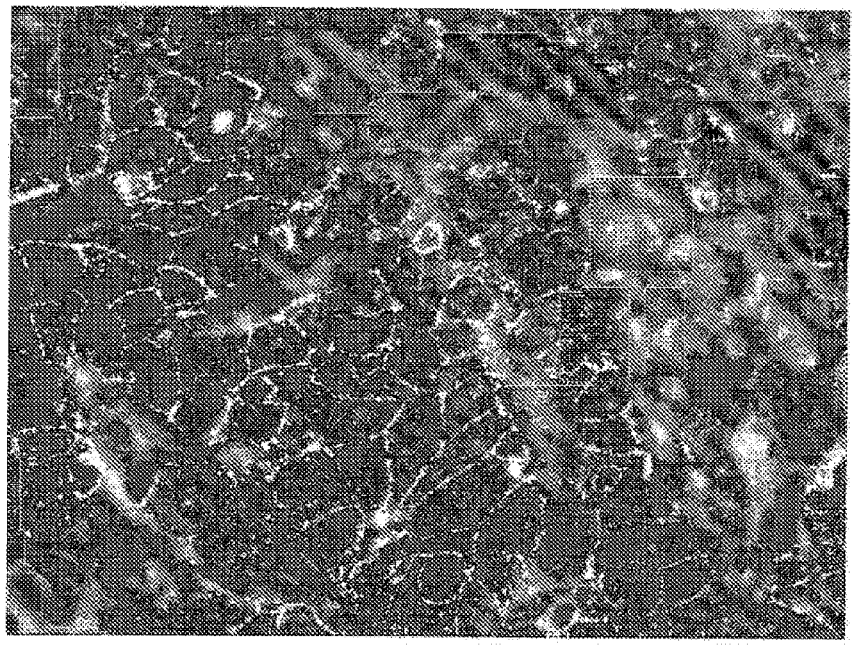

METHOD FOR STAINING TISSUE

CROSS REFERENCE TO RELATED APPLICATION

This Application is a 371 of PCT/JP2013/058701 filed on Mar. 26, 2013 which, in turn, claimed the priority of Japanese Patent Application No. JP2012-080782 filed on Mar. 30, 2012 both applications are incorporated herein by reference.

TECHNICAL FIELD

The present invention relates to a method for staining a tissue. More particularly, the present invention relates to a method for staining a tissue, in which both staining that allows bright field observation and staining that uses a light-emitting substance are carried out.

BACKGROUND ART

Immunohistochemistry (IHC) is widely known as a histological (histochemical) technique in which an antigen in a tissue sample is detected using an antibody. This immunohistochemistry may be referred to as "immunostaining" or the like, from the standpoint of carrying out a color-developing process in order to visualize antigen-antibody reaction which is originally invisible (hereinafter, in the present specification, the term "immunohistochemical staining" may be also used for this immunohistochemistry). Due to its feature of visualizing the location where the antigen-antibody reaction is, the immunohistochemistry is widely used in the fields of medicine and life chemistry for the purpose of detecting the location where a biological substance in a tissue sample is.

In addition, as a histological (histochemical) technique related to the immunohistochemistry, lectin staining is also known. This lectin staining is a technique for detecting a sugar chain in a tissue sample using lectin by using the nature of lectin nonimmunologically and specifically binding to a particular sugar chain, and is widely used in the fields related to sugar chains.

In an IHC method, a staining method that allows bright field observation is widely used as a method for visualizing the location where the antigen-antibody reaction is. Specifically, a technique that uses a substrate to be converted into a pigmentary substance by an enzyme is commonly used. For example, in clinical sites, a method, in which an anti-HER2 antibody bound to a HER2 antigen site in a tissue sample is stained and visualized using diaminobenzidine (DAB), and the expression amount of the HER2 is detected by bright field observation via the visualized anti-HER2 antibody, is widely carried out. This bright field observation has the advantage that, by comprehensively judging from the information obtained in an analog manner which is about the color and so on resulting from the staining, more detailed information on the target molecule can be obtained as compared to the method using a light-emitting substance as described below.

However, there is a problem with the quantitativity of its results, since, in a staining method using an enzyme reaction like the DAB method, the stainability is changed depending on the staining conditions including the reaction time (see, for example, Non-patent Documents 1 and 2). In addition, its criteria lack quantitativity because of their roughness since the staining level is graded in only 4 scores of from 0 to 3, and further the judgment using the criteria depends on the level of skill of the pathologist or the like, which have been problematic.

In the IHC method, a visualization method that uses a substance having a color-developing property in itself (hereinafter also referred to as a "light-emitting substance") is also used, and, for example, phosphors are suitably used therein (immunostaining that uses a phosphor is hereinafter also referred to as "immunofluorescence staining"). According to the visualization technique using a phosphor, quantitative evaluation can be carried out, for the technique has an excellent reproducibility since the change in the stainability depending on the staining conditions including the reaction time of the enzyme is small, and, the location and the expression amount of a biological substance can be digitally analyzed (see, for example, Non-patent Document 2).

However, in clinical sites, the staining methods using DAB or the like which allows bright field observation as described above have been used for many years, and knowhow for evaluating the pathology has been accumulated. Consequently, a skilled pathologist could judge the pathology more rightly and in more detail on the basis of information about the color and so on resulting from the staining, as compared to the case of a method using a light-emitting substance.

Accordingly, there is a problem that, in the case of using only the information obtained by visualization using a light-emitting substance such as a phosphor, quantitativity can be expected but the more right and detailed pathology judgment based on the experiences of the skilled pathologists can not be expected.

In addition, as a method of examination in which a biological substance in a tissue sample is quantitatively detected, fluorescence in situ hybridization method (FISH method), in which gene expression amount is evaluated, is also used in clinical sites. For example, a method, in which a probe for detecting the HER2 gene and a probe for detecting the centromere of chromosome 17 are used; the HER2 gene copy number per chromosome 17 is counted; and, based on the results thereof, whether the HER2 gene has been amplified or not is judged, is carried out.

However, the FISH method is a quantitative examination method, but is not a method by which the expression amount and/or the intracellular localization of a protein are directly evaluated, which has been problematic.

PRIOR ART DOCUMENTS

Non-Patent Documents

[Non-patent Document 1] Rimm D L, Nature Biotechnology, vol. 24, No. 8, pp. 914-916 (2006)
[Non-patent Document 2] Barrow B et al., Journal Clinical Pathology, vol. 64, pp. 208-214 (2011)

SUMMARY OF THE INVENTION

Problems to be Solved by the Invention

In view of the problems in the conventional techniques as described above, an object of the present invention is to provide a method for staining a tissue enabling highly precise staining, by which, regarding the expression amount and/or the location of a biological substance in a tissue sample, both detailed information that can be obtained by the staining that allows bright field observation, and information with a high quantitativity that can be obtained by the staining that uses a light-emitting substance such as a phosphor can be acquired.

Means for Solving the Problems

The present inventors intensively studied in order to attain the object of the present invention to discover that, by carrying out both staining that allows bright field observation and fluorescence staining for the same specific biological substance on one tissue section, information about the expression amount, the localization, and so on of the specific biological substance on the tissue section can be acquired with a high quantitativity and in detail, thereby completing the present invention. In one aspect of the present invention, the present invention comprises the followings to solve at least one of the problems as described above.

[1] A method for staining a tissue, in which both staining that allows bright field observation and fluorescence staining are carried out for the same specific biological substance.

Effects of the Invention

According to the present invention, information about the expression amount, the intracellular localization, and so on of a specific biological substance on a tissue section can be acquired with a high quantitativity and in detail. In addition, double check by both visual evaluation and digital evaluation using the same section can be carried out. Consequently a method which can cover variation in diagnosis by the level of skill of pathologists and enables right judgment on the results can be provided. Specifically, for example, a system in which, after the visual evaluation by physicians, automatic analysis based on bright spots of fluorescence is automatically carried out by a virtual slide system or the like to extract samples whose results therefrom are different from the evaluation by the physicians and propose reevaluation to the physicians can be exemplified. Moreover, a method for judging with a high precision the effectiveness of a pharmaceutical containing an antibody as an ingredient can be provided.

BRIEF DESCRIPTION OF THE DRAWINGS

FIG. 1 is a conceptual diagram showing examples of the constitution of a labeled probe biological substance.

FIG. 2 is a conceptual diagram showing an example of a labeled probe biological substance to which a label used for the staining that allows bright field observation and a fluorescent label are consecutively binding.

FIG. 3 is a conceptual diagram showing an example of a labeled probe biological substance to which a label used for the staining that allows bright field observation and a fluorescent label are consecutively binding.

FIG. 4 is a DAB stain image and a biotinylated TXR-aggregated silica nanoparticle fluorescence stain image in the same visual field, which were obtained in Example 6.

MODE FOR CARRYING OUT THE INVENTION

Modes for carrying out the present invention will now be described in detail, but the present invention is not limited thereto.

In the present invention, a specific biological substance whose expression amount, localization, and so on in a tissue sample is to be detected (in the present invention, this may be referred to as a "biological substance to be detected" or a "specific biological substance") is detected by histochemical staining that uses a "labeled probe biological substance".

As used herein, a "labeled probe biological substance" refers to a complex which comprises a biological substance specifically binding to a specific biological substance (hereinafter referred to as a "probe biological substance"), and a substance capable of visualizing a biological substance (hereinafter referred to as a "label").

In the present invention, "a labeled probe biological substance(s)" is constructed using 2 types of "labels". The first label is a label used for the staining that allows bright field observation (typically, a "pigmentation-inducing label"), and the second label is a label used for the fluorescence staining (typically, a "fluorescent label").

In the present invention, "staining that allows bright field observation" refers to staining in which direct visualization is accomplished in a form visible by an ordinary light microscope without the label being excited by receiving energy from outside (in other words, visible light is reflected). The phrase "direct visualization is accomplished in a form visible" means to make it possible to, without carrying out any secondary process such as development, directly observe the location where the specific binding reaction between biological substances is. The term "pigmentation-inducing label" refers to a label which is a pigmentation-inducing substance as described below, and the term "fluorescent label" refers to a label which is a phosphor as described below.

<Labels, Probe Biological Substance, and Labeled Probe Biological Substance>
<<Labels>>

At the time when the histochemical staining described below is carried out for a tissue section, labels are on the tissue section, and are used to visualize a biological substance to be detected.

In the present invention, as described above, 2 types of "labels" are used. The first label is a label used for the staining that allows bright field observation, and the second label is a label used for the fluorescence staining.

In the present invention, it is suitable to use a pigmentation-inducing substance as the first label used for the staining that allows bright field observation, and a phosphor as the second label used for the fluorescence staining, respectively.

However, they are not particularly limited, as long as they hinder neither the binding reaction between a biological substance to be detected and a probe biological substance specifically binding to said biological substance to be detected, such as antigen-antibody reaction, (hereinafter also referred to as "the specific binding reaction between biological substances"), nor the quantitativity in measurement.

<1. Label Used for Staining that Allows Bright Field Observation>

[Pigmentation-Inducing Substance (Pigmentation-Inducing Label)]

Examples of the label that allows bright field observation of the present invention include pigmentation-inducing substances, in other words, enzymes that change a substrate into a pigmentary chemical species. Examples of such enzymes may include enzymes, including peroxidase such as horseradish peroxidase (HRP), alkaline phosphatase (ALP), glucosidase and the like.

[Substrate Used for Pigmentation]

As a substrate to be converted into a pigmentary substance by an enzyme as described above, substrates which are commonly used as a chromogenic substrate in conventionally known assay methods based on a chromogenic substrate conversion method may be used. Examples of such substrates include, but are not limited to, substrates for oxidoreductases such as a substrate for horseradish peroxidase (HRP), substrates for phosphatases such as a substrate for alkaline phosphatase (ALP), and substrates for glycosidases such as a substrate for β-galactosidase.

Specific examples of a substrate used for an enzyme reaction by HRP include 3,3'-diaminobenzidine (DAB), 3-p-hydroxyphenylpropionic acid (HPPA), ECL plus (trademark), 4-chloro-1-naphthol/4-chloronaphthalen-1-ol, and so on. Among these, DAB is preferably used, since it is widely used from the standpoint of its storage stability and its color different from hematoxylin (blue), which is commonly used for nuclear staining.

Examples of a substrate used for an enzyme reaction by alkaline phosphatase (ALP) include a 5-bromo-4-chloro-3-indolyl phosphate/nitro blue tetrazolium salt (BCIP/NBT), 4-methylumbelliferyl phosphate (MUP), 6,8-difluoro-4-methylumbelliferyl phosphate (DiFMUP), AttoPhos (registered trademark), 9H-(1,3-dichloro-9,9-dimethylacridin-2-one-7-yl)phosphate (DDAOP), and so on.

Examples of a substrate used for an enzyme reaction by β-galactosidase include 5-bromo-4-chloro-β-indolyl-β-D-galactopyranoside (X-gal), 9H-(1,3-dichloro-9,9-dimethylacridin-2-one-7-yl) β-D-galactopyranoside (DDAOG), 4-methylumbelliferyl-β-D-galactoside (MUG), and so on.

<2. Label Used for Fluorescence Staining>

[Phosphor (Fluorescent Label)]

As a label used for the fluorescence staining of the present invention, a light-emitting substance may be used. The "light-emitting substance" is a substance that is excited by receiving energy from outside and then emits light during the transition from the excited state to the ground state, in other words, a substance that emits light by luminescence. Examples of the "energy from outside" include energy by electromagnetic waves, heat, friction, chemical reactions, or the like. Examples of the mode of emitting light include light emission associated with deactivation from an excited singlet state, light emission associated with deactivation from a triplet state, and so on.

In the present invention, as described above, it is appropriate to use a phosphor as the light-emitting substance. Examples of the phosphor include fluorescent substances such as organic fluorescent dyes and semiconductor nanoparticles, and fluorescent aggregates in which multiple fluorescent substances are aggregated, as described in detail below, and so on.

In the present specification, the "phosphor" refers to in general a substance that is excited by irradiation of an X-ray, an ultraviolet ray or a visible ray from outside and then emits light during the transition from the excited state to the ground state. Accordingly, the kind of the mode of the transition from the excited state back to the ground state is not restricted, and therefore, a "phosphor" as used in the present invention may be a substance that emits fluorescence in a narrow sense, which is light emission associated with deactivation from an excited singlet state, or may be a substance that emits phosphorescence, which is light emission associated with deactivation from a triplet state.

The "phosphor" as used in the present invention is also not limited by the emission lifetime after the excitation light is shut out. Therefore, the "phosphor" may be a substance known as a substance that stores light, such as zinc sulfide or strontium aluminate

[Organic Fluorescent Dye]

Examples of the organic fluorescent dye may include fluorescein dye molecules, rhodamine dye molecules, Alexa Fluor (registered trademark, manufactured by Invitrogen Corporation) dye molecules, BODIPY (registered trademark, manufactured by Invitrogen Corporation) dye molecules, Cascade (registered trademark, Invitrogen Corporation) dye molecules, coumarin dye molecules, NBD (registered trademark) dye molecules, pyrene dye molecules, Texas Red (registered trademark) dye molecules, cyanine dye molecules, perylene dye molecules, oxazine dye molecules, and so on.

Specifically, 5-carboxy-fluorescein, 6-carboxy-fluorescein, 5,6-dicarboxy-fluorescein, 6-carboxy-2',4,4',5',7,7'-hexachlorofluorescein, 6-carboxy-2',4,7,7'-tetrachlorofluorescein, 6-carboxy-4',5'-dichloro-2',7'-dimethoxyfluorescein, naphthofluorescein, 5-carboxy-rhodamine, 6-carboxy-rhodamine, 5,6-dicarboxy-rhodamine, rhodamine 6G, tetramethylrhodamine, X-rhodamine, and Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 635, Alexa Fluor 647, Alexa Fluor 660, Alexa Fluor 680, Alexa Fluor 700, Alexa Fluor 750, BODIPY FL, BODIPY TMR, BODIPY 493/503, BODIPY 530/550, BODIPY 558/568, BODIPY 564/570, BODIPY 576/589, BODIPY 581/591, BODIPY 630/650, BODIPY 650/665 (these are all manufactured by Invitrogen Corporation), methoxycoumarin, NBD, pyrene, Cy5, Cy5.5, Cy7, and so on may be included. These may be used alone, or may be used in a form of a mixture of two or more of them.

These organic fluorescent dyes may be used individually, or two or more of them may be used in combination.

[Semiconductor Nanoparticle]

As a semiconductor nanoparticle, any of semiconductor nanoparticles containing a group II-VI compound, a group III-V compound, a group compound, or a group IV element as an ingredient (these are also referred to as "a group II-VI semiconductor nanoparticle", "a group II-V semiconductor nanoparticle", "a group semiconductor nanoparticle", "a group IV semiconductor nanoparticle", respectively) may be used. As used herein, the term "nanoparticle" is used to mean a particle whose size is in the order of nanometers (from 1 nanometer to hundreds nanometers).

Specific examples thereof include, but are not limited to, CdSe, CdS, CdTe, ZnSe, ZnS, ZnTe, InP, InN, InAs, InGaP, GaP, GaAs, CuInS, CuInSe, AgInSe, AgInS, CuInGaS, Si, Ge, and so on.

In the present invention, it is preferable to use a semiconductor nanoparticle as the fluorescent substance, since the location of a biological substance to be detected can be observed in a form of bright spots. These semiconductor nanoparticles may be used individually, or two or more of them may be used in combination.

[Semiconductor Nanoparticle Having Core/Shell Structure]

In addition, in the present invention, a semiconductor nanoparticle having a core/shell structure, in which a semiconductor nanoparticle as described above is used as a core and a shell is provided thereon, may be also used. Hereinafter, throughout the present specification, the notation of the semiconductor nanoparticle having a core/shell structure is as follows: for example, in the case of CdSe as a core and ZnS as a shell, said semiconductor nanoparticle is represented by CdSe/ZnS.

As the semiconductor nanoparticle having a core/shell structure, for example, CdSe/ZnS, CdS/ZnS, InP/ZnS, InGaP/ZnS, Si/SiO$_2$, Si/ZnS, Ge/GeO$_2$, Ge/ZnS, or the like may be used, but the semiconductor nanoparticle having a core/shell structure is not limited to these.

The semiconductor nanoparticle to be used may be one whose surface has been treated by an organic polymer or the like, as needed. Examples thereof include, for example, CdSe/ZnS having surface carboxy groups ("Qdot ITK" (registered trademark), manufactured by Invitrogen Corporation), CdSe/ZnS having surface amino groups ("Qdot ITK" (registered trademark), manufactured by Invitrogen Corporation), and so on

[Rare Earth Phosphor]

Examples of other fluorescent substances that may be used in the present invention include rare earth phosphors. As the rare earth phosphor, for example, neodymium oxide, neodymium chloride, neodymium nitrate, ytterbium oxide, ytterbium chloride, ytterbium nitrate, lanthanum oxide, lanthanum chloride, lanthanum nitrate, yttrium oxide, yttrium chloride, yttrium nitrate, praseodymium chloride, erbium chloride, orthophosphate, ammonium phosphate, ammonium dihydrogen phosphate, or the like may be used.

[Fluorescent Aggregate]

In addition, in the present invention, not only the fluorescent substances as described above, but also a fluorescent aggregate in which multiple fluorescent substances are aggregated may be used as the phosphor. It is preferable to carryout staining of a tissue section using as a phosphor a fluorescent aggregate in which multiple fluorescent substances are aggregated, since the location of a biological substance to be detected can be observed in a form of bright spots even when using a general-purpose microscope (without using a confocal laser microscope).

As used herein, the "fluorescent aggregate in which multiple fluorescent substances are aggregated" refers to an aggregate in which fluorescent substances such as an organic fluorescent dye(s), a semiconductor nanoparticle(s), and/or the like as described above are aggregated in a mode in which they exist inside and/or on the surface of said aggregate. Therefore, the "fluorescent aggregate in which multiple fluorescent substances are aggregated" may be a fluorescent aggregate having a core/shell structure that has a core capable of immobilizing a large number of fluorescent substances and a shell comprising multiple fluorescent substances immobilized on the core, or may be a fluorescent aggregate having a morphology such as a phosphor-containing nanoparticle that has a structure in which multiple fluorescent substances are contained in a base material.

The material constituting the fluorescent aggregate is not particularly limited, and examples thereof may include polystyrene, amino resins, polylactic acid, silica, and so on.

The fluorescent aggregate may be produced by a known method. For example, a silica nanoparticle in which organic fluorescent dyes are aggregated may be synthesized referring to the synthesis of fluorescein isothiocyanate (hereinafter referred to as "FITC")-containing silica particles as described in Langmuir, Vol. 8, p. 2921 (1992). By using a desired organic fluorescent dye instead of FITC, various organic fluorescent dye-aggregated silica nanoparticles can be synthesized.

A silica nanoparticle in which quantum dots are aggregated may be synthesized referring to the synthesis of CdTe-aggregated silica nanoparticles as described in New Journal of Chemistry, Vol. 33, p. 561 (2009).

A polystyrene nanoparticle in which organic fluorescent dyes are aggregated may be produced by using the copolymerization method that uses organic dyes having polymerizable functional groups as described in U.S. Pat. No. 4,326,008 (1982), or the method of impregnating organic fluorescent dyes into polystyrene nanoparticles as described in U.S. Pat. No. 5,326,692 (1992).

A polymer nanoparticle in which quantum dots are aggregated may be produced using the method of impregnating quantum dots into polystyrene nanoparticles as described in Nature Biotechnology, Vol. 19, p. 631 (2001).

The average particle size of the fluorescent aggregate is not particularly limited, but usually from 30 to 800 nm, preferably from 50 to 200 nm. In addition, the coefficient of variation, which shows the variation in the particle size, is also not particularly limited, but usually 20% or less, preferably from 5% to 15%. The average particle size as used herein is the arithmetic mean of the area circle equivalent diameters, which are obtained by taking electron micrographs using a scanning electron microscope (SEM), measuring the cross-sectional area of a sufficient number (for example, 1000) of fluorescent aggregates, calculating diameters of the circles whose areas are equivalent to the measured values, and considering the calculated diameters of the circles as their particle sizes; and the coefficient of variation is the value that is calculated from the particle size distribution measured as described above (100×the standard deviation/the average particle size of the particle sizes). In other words, in the present specification, the "average particle size" means a number average particle size.

Among the above-described phosphors, fluorescent aggregates in which multiple fluorescent substances are aggregated are especially preferably used, since a high emission intensity is easy to be obtained, and an excellent quantitativity can be obtained.

<Biological Substance to be Detected>

The biological substance to be detected by the tissue staining method of the present invention is not particularly limited, but is one also functioning as a target biological substance to which a probe biological substance as described below specifically binds, for visualization by a label as described below is carried out via the specific binding reaction between these biological substances, such as antigen-antibody reaction.

In the tissue staining method of the present invention, as the histochemical staining described below, immunohistochemical staining (immunostaining) is suitably used, and accordingly, typical examples of the "biological substance to be detected" include a biological substance functioning as an antigen against an antibody.

In the present invention, the term "antigen" refers to a biological substance, especially, a molecule or a molecular fragment, and examples of such a "molecule" or a "molecular fragment" include, for example, nucleic acids (DNAs, RNAs, polynucleotides, oligonucleotides, PNAs (peptide nucleic acids) and the like which may be either single-stranded or double-stranded, or nucleosides, nucleotides and modified molecules thereof), proteins (polypeptides, oligopeptides, and the like), amino acids (including modified amino acids), carbohydrates (oligosaccharides, polysaccharides, sugar chains, and the like), lipids, or modified molecules and complexes thereof, and so on.

Specifically, it may be a tumor marker, a signal transducer, a hormone, or the like, and is not particularly limited. For example, in case where an antibody drug used as an anticancer agent is used as the antibody, examples of suitable target antigen include growth regulatory factors, metastasis regulatory factors, growth regulatory factor receptors and metastasis regulatory factor receptors in cancer, and so on.

Among such growth regulatory factors, metastasis regulatory factors, growth regulatory factor receptors and metastasis regulatory factor receptors, examples of the growth regulatory factors and receptors thereof in cancer may include, for example, cell growth factors and receptors thereof, such as epidermal growth factor(EGF), EGF receptor(EGFR), platelet-derived growth factor(PDGF), PDGF receptor (PDGFR), insulin-like growth factor (IGF), IGF receptor (IGFR), fibroblast growth factor(FGF), FGF receptor (FGFR), vascular endothelial growth factor (VEGF), VEGF receptor (VEGFR), hepatocyte growth factor (HGF), HGF receptor (HGFR), neurotrophic factor (NT: Neurotrophin), transforming growth factor-β (TGFβ) family, HER2; and factors that control cell cycle, such as cyclin, cyclin-dependent kinase (CDK), cyclin A, cyclin B, cyclin D, cyclin E, CDK1, CDK2, CDK4, CDK6, p16INK, p15, p21, p27, RB (Retinoblastoma). In addition, examples of the metastasis regulatory factors and receptors thereof in cancer may include, for example, matrix metalloprotease 1(MMP1), matrix metalloprotease 2(MMP2), PAR1 (protease activated receptor 1), CXCR4 (chemokine [C-X-C motif] receptor 4), CCR7 (chemokine [C-C motif] receptor 7), and so on. Among these, since trastuzumab which is targeted to HER2 is widely used, HER2 can be suitably exemplified.

Further, not only the antigens related to cancer but also inflammatory cytokines including TNF-α (Tumor Necrosis Factor α), IL-6 (Interleukin-6) receptors, and the like, virus-associated molecules including RSV F protein and the like, and so on may be a target of detection by the staining method of the present invention.

On the other hand, in the tissue staining method of the present invention, if, as the histochemical staining described below, a technique other than immunohistochemical staining is used, then the "biological substance to be detected" is not necessarily required to be one functioning as an antigen. For example, in cases where lectin staining is used as the histochemical staining described below, examples of the "biological substance to be detected" include carbohydrates (oligosaccharides, polysaccharides, sugar chains, and the like), or modified molecules and complexes thereof, and so on, and the "biological substance to be detected" may be a tumor marker, a signal transducer, a hormone, or the like.

In the present specification, "the same specific biological substance" means not only that the type of the biological substance to be detected is the same, but also that the biological substance to be detected itself is the same molecule or the same molecular fragment.

<<Probe Biological Substance>>

In the tissue staining method of the present invention, when the histochemical staining as described below is carried out for a tissue section, a "probe biological substance" specifically binding to said "biological substance to be detected" is used as a vehicle for introducing a label as described above onto a "biological substance to be detected" that is present on said tissue section. Examples of the probe biological substance used in the tissue staining method of the present invention include antibodies, lectins, and so on.

In the present invention, the term "antibody" is used to include arbitrary antibody fragments or derivatives, and includes a variety of antibodies such as Fab, Fab'$_2$, CDR, humanized antibodies, multifunctional antibodies, single-chain antibodies (ScFv).

In the present invention, for example, an antibody that is a component of an antibody drug may be used for immunohistochemical staining of a tissue section. As the antibody drug, for example, an antibody drug commonly used for treating autoimmune diseases including rheumatoid arthritis, malignant tumors including cancer, viral infectious diseases, or the like may be used.

Representative antibody drugs that have been clinically used are shown in Table 1 below. In Table 1, there is the following relationship: for example, "Herceptin" is an antibody drug, and "trastuzumab" is an antibody contained therein as a component thereof (i.e., an antibody drug-constituting antibody).

TABLE 1

Representative Antibody Drugs

| Target Disease | Generic Name | Trade Name | Target Molecule |
|---|---|---|---|
| Cancer and Related Disease | Rituximab | Rituxan (registered trademark) | CD20 |
| | Gemtuzumab (Gemutuzumab) | Mylotarg (registered trademark) | CD33 |
| | Alemtuzumab | Campath (registered trademark) | CD52 |
| | Ibritumomab | Zevalin (registered trademark) | CD20 |
| | Tositumomab | Bexxar (registered trademark) | CD20 |
| | Trastuzumab | Herceptin (registered trademark) | HER2 |
| | Bevacizumab | Avastin (registered trademark) | VEGF |
| | Cetuximab | Erbitux (registered trademark) | EGF Receptor |
| | Panitumumab | Vectibix (registered trademark) | EGF Receptor |
| Autoimmune Disease | Infliximab | Remicade (registered trademark) | TNF-α |
| Infectious Disease | Palivizumab | Synagis (registered trademark) | RSVF Protein |

Among the antibody drugs as shown in Table 1 above, gemtuzumab has used in a form of gemtuzumab ozogamicin (Gemutuzumab-Ozogamicin), in which gemtuzumab is binding calicheamicin, an antitumor active substance.

Among the antibody drugs as shown in Table 1 above, especially the antibody drug containing trastuzumab as a component (i.e., Herceptin (registered trademark)) is suitably used.

Further, examples of cancer to which the staining method of the present invention is to be applied may include large bowel cancer, rectal cancer, renal cancer, breast cancer, prostate cancer, uterine cancer, ovarian cancer, endometrial cancer, esophageal cancer, blood cancer, liver cancer, pancreatic cancer, skin cancer, lung cancer, breast cancer, and so on.

In the present invention, the term "lectin" is used as a general term for proteins that specifically bind to a sugar chain. Examples of the lectin include "R-type lectins" which are related to ricin B chain and which are found in the kingdoms of all organisms including bacteria; "calnexin and calreticulin" which are present in the whole eukaryotic organisms and are involved in folding of glycoproteins; "C-type lectins" which are calcium-requiring and which are present widely in multicellular animals and include a large number of representative lectins such as "selectin", "collectin", and the like; "galectins" which are widely distributed in the animal kingdom and exhibit specificity to galactose; "legume lectins" which form a large family in legumes; and "L-type lectins" which have structural similarity to legume lectins and are involved in intracellular transport in animals; "P-type lectins" which have an ability to bind to mannose 6-phosphate and which are involved in intracellular transport of lysosomal enzymes; "annexins" which bind to an acidic sugar chain such as glycosaminoglycan; "I-type lectins" which belong to the immunoglobulin superfamily and include "siglec"; and so on.

Representative lectins are shown in Table 2 below.

TABLE 2

Representative Lectins

| | Lectin | | Specificity |
|---|---|---|---|
| Abbreviation | Popular Name | Origin | Sugar Chain |
| Con A | Concanavalin A | *Canavalia ensiformis* | Manα1→6(Manα1→3)Man |
| PNA | Peanut Lectin | *Arachis hypogaea* | Galβ1→3GalNAc |
| SBA | Soybean Lectin | *Glycine max* | GalNAcα1→3Gal |
| UEA-I | Gorse Lectin | *Ulex europaeus* | Fucα1→2Galβ1→4GlcNAc |

<<Labeled Probe Biological Substance>>

In the tissue staining method of the present invention, a complex, by which both of a label used for the staining that allows bright field observation and a fluorescent label used for the fluorescence staining are directly or indirectly binding to the same specific biological substance via a probe biological substance(s) during observation of a tissue, i.e., a "labeled probe biological substance", is made to form.

The mode of forming such a labeled probe biological substance is not particularly limited, but examples thereof include the modes as described below.

FIG. 1, the first mode, Mode 1, of the labeled probe biological substance 20 is one in which a label 30 used for the staining that allows bright field observation, such as a pigmentation-inducing substance, and a fluorescent label 40 used for the fluorescence staining are consecutively binding to probe 20 (in other words, the probe biological substance for making these 2 types of labels bind to the specific biological substance 10 is shared thereby) (FIG. 1: Mode 1). In FIG. 1, Mode 2, the second mode of the labeled probe biological substance 20 is one in which a label 30 used for the staining that allows bright field observation, such as a pigmentation-inducing substance, and a fluorescent label 40 used for the fluorescence staining are each contained in different labeled probe biological substances 20 (in other words, the probe biological substances for making these 2 types of labels bind to the specific biological substance 10 are not shared thereby) (FIG. 1: Mode 2). Among these, the first mode in which, due to the sharing of a probe biological substance 20, the 2 types of labels 30, 40 can be made to bind to a specific biological substance 10 without interference with each other by failure of binding or the like caused by a steric hindrance or the like, is more preferable, since the stainability in bright field observation and the stainability in fluorescence observation, for a specific biological substance in a tissue, (e.g., the number of the fluorescence signal bright spots per cell) are excellent.

As used herein, the term "consecutively bind" in the first mode described above means that a label used for the staining that allows bright field observation such as a pigmentation-inducing substance, and a label which is a light-emitting substance such as a phosphor are directly or indirectly binding to one labeled probe biological substance in the binding manners as exemplified below. The term "indirectly bind" means to bind via some molecule. Therefore, in case of consecutively binding, a pigmentation-inducing substance and a light-emitting substance are contained in one labeled probe biological substance.

In this case, it is appropriate that the label used for the staining that allows bright field observation, and the label which is a light-emitting substance such as a phosphor are those that do not compete with each other in binding to a probe biological substance. If competition occurs, for example, in case where the probe biological substance has been modified with one molecule (for example, biotin or the like) and both labels are each modified with a molecule that binds to said molecule (for example, avidin or the like), then the same specific biological substance can not be labeled with both of the label used for the staining that allows bright field observation and the label which is a light-emitting substance such as a phosphor, and will be labeled with either one of them. As a result, the stainability in bright field observation and the stainability in fluorescence observation for a specific biological substance in a tissue will both be greatly decreased as respectively compared with the stainability in case of staining using the label used for the staining that allows bright field observation alone and the stainability in case of staining using the label which is a light-emitting substance such as a phosphor alone.

On the other hand, when a label used for the staining that allows bright field observation such as a pigmentation-inducing substance, and a label which is a light-emitting substance such as a phosphor are contained in different labeled probe biological substances, it is appropriate that probe biological substances contained in these labeled probe biological substances are those that recognize different sites of the same specific biological substance and do not compete with each other in the specific binding reaction between biological substances, from the standpoint of maintaining both of the stainability in bright field observation and the stainability in fluorescence observation for a specific biological substance in a tissue (e.g., the number of the fluorescence signal bright spots per cell) at a high level. For example, if the probe biological substances contained in these labeled probe biological substances are those that recognize the same site of the same specific biological substance and competition occurs in the specific binding reaction between these biological substances, then the same specific biological substance can not be labeled with both of the label used for the staining that allows bright field observation and the label which is a light-emitting substance such as a phosphor, and will be labeled with either one of them. As a result, the stainability in bright field observation and the stainability in fluorescence observation for a specific biological substance in a tissue will both be greatly decreased as respectively compared with the stainability in case of staining using the label used for the staining that allows bright field observation alone and the stainability in case of staining using the label which is a light-emitting substance such as a phosphor alone.

The labeled probe biological substance has a structure in which the probe biological substance (for example, an antibody, a lectin, or the like) and a label(s) are binding in an appropriate binding manner such as a covalent bond, an ionic bond, a hydrogen bond, a coordinate bond, a physical adsorption, a chemical adsorption, or the like. From the standpoint of the strength of binding force, it is preferable to have a structure in which these are binding via a covalent bond such as an amide bond, an ester bond, an imide bond, a bond obtained by using addition of a thiol group to a maleimide group, or a biotin-avidin bond or a biotin-streptavidin bond. Especially, from the standpoint of the strength of binding force and the specificity of binding, it is more preferable to have a structure in which these are binding via a biotin-avidin bond or a biotin-streptavidin bond.

Such a labeled probe biological substance may be obtained by binding a label(s) to a probe biological substance as described above according to a conventional method. Examples of a specific method for labeling may include a method via an antibody having a specific affinity for a probe biological substance as described above (an secondary antibody), a biotin-avidin method, a method by using the coupling reaction between a thiol group and a maleimide group, an existing method that uses a chemical linker, a cross-linking reaction method that uses a cross-linking agent (1-ethyl-3-(3-dimethylaminopropyl) carbodiimide (EDC) or the like), an ionic bond method, and so on. However, in case where the probe biological substance is a humanized antibody or a human antibody, among these, a method by using the coupling reaction between a thiol group and a maleimide group for an antibody or avidin can be suitably exemplified.

Specific forming procedures are, for example, as follows.

First, a first linking group is introduced onto a probe biological substance, and a second linking group capable of binding to the first linking group is introduced onto a label. In this case, a linker having an appropriate chain length may respectively exist between the first linking group and the probe biological substance, and, between the second linking group and the label. The first and second linking groups may be a chemical functional group such as a carboxyl group, an amino group, an aldehyde group, a thiol group, a maleimide group, or the like, or may be a molecule like biotin, avidin, or streptavidin. If a secondary antibody is used as said second linking group, said first linking group may be a site that constitutes the probe biological substance and is a site other than the site recognizing a "biological substance to be detected".

Suitable examples of the probe biological substance onto which a first linking group has been introduced, i.e., a linking group-containing probe biological substance that comprises a first linking group and a probe biological substance, include biotinylated probe biological substances such as biotinylated antibodies, biotinylated lectins, or the like. On the other hand, suitable examples of the label onto which a second linking group has been introduced, i.e., a linking group-containing label that comprises a second linking group and a label as described above, include avidin-bound labels or streptavidin-bound labels. However, the above examples are not intended to prevent the use of an avidinylated probe biological substance or a streptavidinylated probe biological substance as the probe biological substance onto which a first linking group has been introduced and the use of a biotin-bound label as the label onto which a second linking group has been introduced. In addition, the above examples are also not intended to prevent the use of those onto which chemical functional groups have been introduced instead of biotin or avidin (or streptavidin) as a first linking group in the probe biological substance onto which a first linking group has been introduced and a second linking group in the label onto which a second linking group has been introduced.

Next, the probe biological substance onto which a first linking group has been introduced and the label onto which a second linking group has been introduced are made to react to obtain a labeled probe biological substance.

The labeled probe biological substance may be one that is prepared in advance, in the absence of a tissue to be stained, by reacting a probe biological substance onto which a first linking group has been introduced and a label onto which a second linking group has been introduced. Alternatively, the labeled probe biological substance may be one that is formed in a staining step by allowing an un-labeled probe biological substance onto which a first linking group has been introduced to react with a tissue, and thereafter reacting the probe biological substance integrated with said tissue with a label onto which a second linking group has been introduced.

The labeled probe biological substance as described above may be one in which the labeling is via a greater number of linking groups. For example, the labeled probe biological substance may be one which is formed by further introducing a third linking group onto the substance onto which a second linking group has been introduced, and reacting thereto a fourth linking group that can bind to the third linking group, and, any label onto which a fifth linking group has been introduced, and, another label onto which a sixth linking group that can bind to the fifth linking group has been introduced.

Examples of such labeled probe biological substance include, for example, in FIG. 2, one that comprises an antibody 21 that recognizes a specific biological substance 10, a biotinylated antibody 50 that recognizes said antibody 21, a streptavidinylated peroxidase label 70-31, and, a fluorescent label 40 to which an antibody 23 that recognizes peroxidase 31 and binds thereto is binding (FIG. 2: Mode 1A).

Further, in a case as described above, the fourth linking group and the fifth linking group, or, the third linking group and the sixth linking group may be the same linking group, respectively. In FIG. 3, Examples of such labeled probe biological substance include, for example, one that comprises an antibody 21 that recognizes a specific biological substance 10 and binds thereto, a biotinylated antibody 50-80 that recognizes said antibody and binds thereto, a streptavidinylated peroxidase label 70-31, and, a biotinylated fluorescent label 80-40 (FIG. 3: Mode 1B). Such Mode 1B is more preferable mode, since the fluorescent labels can be introduced onto the labeled probe biological substance in a manner whose risk of impairing the function of peroxidase is smaller than that of the above-described Mode 1A, and from the standpoint that biotinylated fluorescent labels have been widely used and are readily available, and so on.

<Histochemical Staining Method>

(1) Histochemical Staining Step

In the method for staining a tissue according to the present invention, the histochemical staining step is a step of carrying out histochemical staining for a tissue section. In other words, the histochemical staining step is a step of reacting a tissue section and a labeled probe biological substance obtained by introducing a label onto a substance that recognizes a biological substance to be detected, and visualizing a specific biological substance that is present on said tissue section via the specific binding reaction between these biological substances. In the present invention, the histochemical staining such as immunohistochemical staining or lectin staining may be carried out by a conventionally known technique.

The method for producing sections to which the tissue staining method of the present invention can apply is not particularly limited, and sections produced by a known method may be used. For example, in cases where paraffin-embedded sections, which have been widely used as pathologic sections, are used as a tissue section, the histochemical staining may be carried out by the procedure as described below.

(1-1) Deparaffinization Treatment Step

A pathologic section is immersed in a container containing xylene to remove paraffin. The temperature is not particularly limited, but this may be carried out at room temperature. The immersion time is preferably from 3 minutes to 30 minutes. Further, xylene may be replaced during the immersion as needed.

Next, the pathologic section is immersed in a container containing ethanol to remove xylene. The temperature is not particularly limited, but this may be carried out at room temperature. The immersion time is preferably from 3 minutes to 30 minutes. Further, ethanol may be replaced during the immersion as needed.

The pathologic section is immersed in a container containing water to remove ethanol. The temperature is not particularly limited, but this may be carried out at room temperature. The immersion time is preferably from 3 minutes to 30 minutes. Further, water may be replaced during the immersion as needed.

(1-2) Activation Treatment Step

If immunohistochemical staining is carried out as the histochemical staining, it is preferable to carry out activation treatment for a biological substance of interest in accord with a known method. The conditions for the activation are not particularly restricted, but as an activation solution, a 0.01 M (molar concentration, mol/L, the same applies hereinafter) citrate buffer solution (pH 6.0), a 1 mM ethylenediaminetetraacetic acid (EDTA) solution (pH 8.0), 5% urea, a 0.1 M Tris-HCl buffer solution, and/or the like may be used. As a heating apparatus, an autoclave, a microwave, a pressure cooker, a water bath, and/or the like may be used. The temperature is not particularly limited, but this may be carried out at room temperature. Or, this may be carried out at a temperature of from 50° C. to 130° C. for a period of from 5 to 30 minutes.

Next, the section after the activation treatment is immersed in a container containing PBS to wash it. The temperature is not particularly limited, but this may be carried out at room temperature. The immersion time is preferably from 3 minutes to 30 minutes. Further, PBS may be replaced during the immersion as needed.

(1-3) Staining Treatment Step by Labeled Probe Biological Substance

In the present invention, both staining that allows bright field observation and staining that uses a light-emitting substance are carried out for the same specific biological substance. Although the order thereof (before and after) is not restricted, from the standpoint of increasing the sensitivity in bright field observation, it is preferable to make a pigmentation-inducing label and a fluorescent label bind to the same specific biological substance, and thereafter add thereto a substrate to be used for pigmentation to allow color development.

As the staining treatment step by a labeled probe biological substance, a step of preparing a PBS dispersion of a labeled probe biological substance as described above, and placing it on the pathologic section to react with a biological substance to be detected is suitably carried out.

When immunohistochemical staining (immunostaining) is carried out as the histochemical staining, the staining may be carried out by preparing a PBS dispersion of an antibody as a probe biological substance, placing it on the pathologic section to allow it to bind to a biological substance to be detected, and making a label onto which a site that binds to the antibody has been introduced further bind to the antibody. Alternatively, the staining may be also carried out by reacting the antibody and the label before placing them on the pathologic section to prepare a labeled probe biological substance, and placing it on the pathologic section.

When the labeled probe biological substance is constituted of a greater number of molecules, the histochemical staining of the present invention can be carried out by preparing PBS dispersions of those molecules, successively placing them in an appropriate order on the pathologic section, allowing them to react, and thereby preparing a labeled probe biological substance which binds to a biological substance to be detected. Also in this case, the staining may be carried out by reacting the constituents of the labeled biological probe that comprises an antibody(ies) and labels before placing them on the pathologic section to prepare a labeled probe biological substance, and placing it on the pathologic section.

When lectin staining is carried out as the histochemical staining, the staining may be carried out by performing the reaction as described above using lectin instead of the antibody.

When two or more kinds of specific biological substances are targets of the staining, the staining may be carried out by preparing PBS dispersions of each of "probe biological substances" individually corresponding to these specific biological substances, and pigmentation-inducing labels different by the corresponding specific biological substances, and fluorescent labels, and placing them on the pathologic section to allow them to react with each biological substance of interest. When placing on the pathologic section, those PBS dispersions of each of the labeled probe biological substances may be placed on after combining them in advance, or may be separately and successively placed on. In either case, it is more preferable to use labeled probe biological substances that individually have appropriate linking groups different by the corresponding specific biological substances, from the standpoint of distinguishing the different specific biological substances.

The reaction temperature is not particularly limited, but this may be carried out at room temperature. The reaction time is preferably from 30 minutes to 24 hours. In addition, it is preferable to add dropwise a known blocking agent such as a BSA-containing PBS or the like before carrying out the staining.

Next, the section after the staining is immersed in a container containing PBS to remove unreacted labels. The temperature is not particularly limited, but this may be carried out at room temperature. The immersion time is preferably from 3 minutes to 30 minutes. PBS may be replaced during the immersion as needed.

(2) Fixation Treatment Step

The fixation treatment step optionally carried out in the tissue staining method of the present invention is a step of fixing the labeled probe biological substance(s) introduced by the histochemical staining step as described above on the tissue section.

In the tissue staining method of the present invention, in case where the morphological observation and staining step (3) as described below is carried out after the histochemical staining step (1) as described above, the stained tissue section obtained by the histochemical staining step may be directly subjected to the morphological observation and staining step. However, from the standpoint that reduction in the emission intensity of the phosphor which is introduced as a label onto the tissue section after the morphological observation and staining can be suppressed, it is preferable to go through the step of carrying out the fixation treatment after carrying out the histochemical staining and before carrying out the morphological observation and staining.

Examples of a fixation treatment solution used in the present invention include cross-linking agents, cell membrane permeable substances and so on, such as formalin, paraformaldehyde, glutaraldehyde, acetone, ethanol, methanol or the like.

In the present invention, the fixation treatment may be carried out by a conventionally known technique. Specifically, the fixation treatment may be carried out by immersing the stained tissue section obtained by the histochemical staining step in such a fixation treatment solution. For example, this may be carried out by immersing the stained tissue section obtained by the histochemical staining step in a dilute paraformaldehyde aqueous solution for a period of from about several minutes to several hours.

(3) Morphological Observation and Staining Step

For example in cases of observing the morphology of a tissue specimen, if needed, the morphological observation and staining step may be performed. Examples of the morphological observation and staining method include, representatively, hematoxylin eosin staining (HE staining) which uses 2 dyes, hematoxylin and eosin, but also include, for example, other morphological observation and staining, such as Papanicolaou staining (Pap staining), which is used for cytodiagnosis.

However, in case of eosin, or an eosin analog, or a dye having an absorption wavelength and an emission wavelength similar to those of eosin, the peak of the emission wavelength of autofluorescence may be adjacent to the peak of the emission wavelength of the fluorescent label(s). Therefore, in the present invention, it is preferable to carry out the morphological observation and staining by hematoxylin or the like alone.

In HE staining, hematoxylin staining stains cell nuclei, calcified parts, cartilaginous tissues, bacteria, and mucus into color from livid to pale blue; eosin staining stains cytoplasm, stroma, various types of fibers, erythrocytes, keratinocytes into color from red to deep red. In other morphological observation and staining, a hematoxylin analog or a dye having an absorption wavelength similar to those of hematoxylin stains cell nuclei, calcified parts, cartilaginous tissues, bacteria, and mucus into color from livid to pale blue, and an eosin analog or a dye having an absorption wavelength and an emission wavelength similar to those of eosin stains cytoplasm, stroma, various types of fibers, erythrocytes, keratinocytes into color from red to deep red.

(4) Observation Step

In the present invention, the observation step can be carried out after the above-described steps (1) to (3). The order of the following observation steps (i.e., which is first) is not restricted.

(4-1) Bright Field Observation Step

The bright field observation step is a step of irradiating an illumination light to the tissue section stained by the above-described steps, observing the pigment in the tissue section resulting from the pigmentation, and acquiring information about the distribution of the "biological substance to be detected" as described above in the cell or in the tissue (hereinafter referred to as "biomolecule distribution information"). When immunohistochemical staining is carried out as the histochemical staining, said "biomolecule distribution information" is acquired as information about the distribution of a particular antigen molecule in the cell or in the tissue; and when lectin staining is carried out as the histochemical staining, said "biomolecule distribution information" is acquired as information about the distribution of a particular sugar chain, or a modified molecule or a complex thereof in the cell or in the tissue.

Further, in the bright field observation step, information about the morphology of the tissue specimen which can be obtained by the morphological observation and staining as described above (hereinafter referred to as "cell morphology information") can be acquired.

This bright field observation may be performed by a common method. For example, in the bright field observation in case where histochemical staining is carried out in case of breast cancer by using HER2 protein as the "biological substance to be detected", the observation of the positive stain image, the positive stain intensity, and/or the positive cell rate for the HER2 protein in the cancer cells in the sample tissue is carried out by using a 4× objective lens on a light microscope under irradiation by an appropriate illumination light. Next, the objective lens is switched to a 10× objective lens, and then whether the localization of the positive findings is in the cell membrane or in the cytoplasm is confirmed. If needed, further search is carried out by using a 20× objective lens.

In this step, the biomolecule distribution information and the cell morphology information may be acquired from the lens barrel of the microscope so as to perform speedy observation, or may be acquired by making the images shot by a camera attached to the microscope to be displayed on a display means (such as a monitor), and observing the displayed images.

(4-2) Light-Emitting Substance Observation Step

The light-emitting substance observation step is a step of irradiating an excitation light to the tissue section stained by the above-described steps, and thereby acquiring biomolecule distribution information based on the fluorescence which is emitted from the fluorescent label as described above.

The excitation light as described above is not particularly limited, as long as it is one that has an appropriate wavelength by which the fluorescent substance constituting a label can emit a fluorescence of a desired wavelength. And, the means for irradiating the excitation light is also not particularly limited. For example, an excitation light of an appropriate wavelength and an appropriate output power may be irradiated from a laser light source provided on a fluorescent microscope to the stained tissue section, if needed, by using a filter selectively transmit a light of a prescribed wavelength.

The excitation light as described above is not particularly limited, as long as the fluorescence emitted by the label can be distinguished from the autofluorescence of the tissue section. However, from the standpoint that fluorescence can be visually observed, absorption by the substrate used in the staining that allows bright field observation (for example, diaminobenzidine) is avoided, and the intensity of autofluorescence from the tissue section is prevented from getting too high, it is preferable for the excitation light as described above to have a wavelength of from 450 nm to 700 nm. As a fluorescent substance constituting a phosphor used as the fluorescent label as described above, one that emits, by said excitation light, a fluorescence having a peak in the range of not less than 480 nm, preferably in the range of from 580 to 690 nm is used (accordingly, fluorescence having an emission wavelength within these ranges is to be measured).

The biomolecule distribution information and the cell morphology information in the light-emitting substance observation step can be acquired in the same visual field. Therefore, it is suitable to set such that both of the autofluorescence of the tissue section and the fluorescence emitted by the label, which are obtained from one stained section, are included in the same visual field; distinguishably recognize them; and, based on each of them, acquire cell morphology information and biomolecule distribution information. Of course, if needed, this may be carried out, for example, by using an appropriate filter that can sufficiently reduce either one of the autofluorescence of the tissue section and the fluorescence emitted by the label, and thereby acquiring only the cell morphology information in one visual field, and thereafter acquiring the biomolecule distribution information in another visual field.

In this step, the biomolecule distribution information and the cell morphology information may be acquired from the lens barrel of the (fluorescent) microscope so as to perform speedy observation, or may be acquired by making the images shot by a camera attached to the (fluorescent) microscope to be displayed on a display means (such as a monitor), and observing the displayed images. Although it depends on the fluorescent substance constituting a phosphor used as a label, even if biomolecule distribution information can not be sufficiently acquired visually from the lens barrel of the microscope, it is sometimes possible to acquire biomolecule distribution information from the images shot by a camera.

Examples of acquiring the biomolecule distribution information include, for example, measuring the number of molecules of the "biological substance to be detected" per cell, or the density of the "biological substance to be detected" (i.e., the number of molecules of the "biological substance to be detected" per unit volume), based on the number of the bright spots or the luminescence brightness of the fluorescence. An excitation light source and an optical filter(s) for fluorescence detection, which correspond to the absorption maximum wavelength and the fluorescence wavelength of the fluorescent substance constituting a phosphor used as a label, may be selected. It is suitable to use a commercially available image analysis software (for example, a software automatically measuring all bright spots "G-Count" (manufactured by G-Angstrom K.K.)) for the measurement of the number of the bright spots or the luminescence brightness, but the measuring means is not particularly limited.

EXAMPLES

The present invention will now be described more concretely by way of Examples, but the scope of the present invention is not limited thereto.
<1. Production of Label>

Synthesis of Fluorescent Aggregate

Synthesis Example 1

FITC-Aggregated Silica Nanoparticle

In N,N-dimethylformamide (DMF), 6.6 mg of amino reactive FITC (manufactured by DOJINDO LABORATORIES) and 3 µL of 3-aminopropyltrimethoxysilane (manufactured by Shin-Etsu Silicone: KBM903) were mixed to obtain an organoalkoxysilane compound.

Then, 0.6 mL of the obtained organoalkoxysilane compound was mixed with 48 mL of ethanol, 0.6 mL of tetraethoxysilane (TEOS), 2 mL of water, and 2 mL of 28% aqueous ammonia for 3 hours.

The mixture produced in the above-described step was centrifuged at 10,000 G for 20 minutes, and the supernatant was removed. Ethanol was added thereto to disperse the precipitate, and centrifugation was carried out again. Further, by the same procedure, washing was carried out twice with ethanol and twice with pure water. As a result, 10 mg of an FITC-aggregated silica nanoparticle was obtained as a fluorescent aggregate.

By performing SEM observation for 1000 of the obtained FITC-aggregated silica nanoparticle, it was found that the average particle size was 104 nm and the coefficient of variation was 12%, respectively.

Synthesis Example 2

TXR-Aggregated Silica Nanoparticle

Using Texas Red (manufactured by DOJINDO LABORATORIES, hereinafter referred to as "TXR") instead of amino reactive FITC in Synthesis Example 1, the same synthesis was carried out, and 10 mg of a TXR-aggregated silica nanoparticle was obtained. By performing SEM observation for 1000 of the obtained TXR-aggregated silica nanoparticle, it was found that the average particle size was 106 nm and the coefficient of variation was 11%.

Synthesis Example 3

Semiconductor Nanoparticle (Qdot605)-Aggregated Silica Nanoparticle

To 10 µL of a CdSe/ZnS decane dispersion ("Qdot605" (registered trademark), manufactured by Invitrogen Corporation), 0.1 mg of TEOS, 0.01 mL of ethanol, 0.03 mL of concentrated aqueous ammonia were added, and the mixture was stirred for 3 hours to carry out hydrolysis.

The mixture obtained in the above-described step was centrifuged at 10,000 G for 20 minutes, and the supernatant was removed. Ethanol was added thereto to disperse the precipitate, and centrifugation was carried out again. Further, by the same procedure, washing was carried out twice with ethanol and twice with pure water. As a result, 40 mg of a Qdot605-aggregated silica nanoparticle was obtained as a fluorescent aggregate.

By performing SEM observation for 1000 of the obtained Qdot605-aggregated silica nanoparticle, it was found that the average particle size was 108 nm and the coefficient of variation was 14%.

Production of Biotinylated Fluorescent Aggregate

Synthesis Example 4

Biotinylated FITC-Aggregated Silica Nanoparticle

Binding of biotin to the FITC-aggregated silica nanoparticle synthesized in Synthesis Example 1 was carried out according to the following procedure to obtain a biotinylated FITC-aggregated silica nanoparticle.

In 1 mL of ethanol, the fluorescent aggregate was dissolved up to 3 nM, and 0.1 µL of 3-aminopropyltrimethoxysilane was added thereto, and thereafter a reaction at room temperature for 1 hour was carried out. The obtained solution was centrifuged at 10,000 G for 20 minutes, and the supernatant was removed. Thereafter, ethanol was added thereto to disperse the precipitate, and centrifugation was carried out again. By the same procedure, washing was carried out 3 times to obtain a fluorescent aggregate for biotin binding.

In phosphate buffered saline (PBS) containing 2 mM ethylenediaminetetraacetic acid (EDTA), the fluorescent aggregate was dissolved to adjust it up to 3 nM. To this solution, biotinylated polyethyleneglycol ("NHS-dPEG-Biotin" (registered trademark), manufactured by TOYOBO: QB10198a, PEG chain length: 12) was mixed so as to attain a final concentration of 10 mM, and a reaction for 1 hour was carried out. This mixture was centrifuged at 10,000 G for 20 minutes, and the supernatant was removed. Thereafter, PBS containing 2 mM. EDTA was added thereto to disperse the precipitate, and centrifugation was carried out again. Further, by the same procedure, washing was carried out 3 times to obtain a biotinylated FITC-aggregated nanoparticle.

Synthesis Example 5

Biotinylated TXR-Aggregated Silica Nanoparticle

A biotinylated TXR-aggregated silica nanoparticle was synthesized in the same manner as in Synthesis Example 4 except that the TXR-aggregated silica nanoparticle synthesized in Synthesis Example 2 was used instead of the FITC-aggregated silica nanoparticle.

Synthesis Example 6

Biotinylated Qdot605-Aggregated Silica Nanoparticle

A biotinylated Qdot605-aggregated silica nanoparticle was synthesized in the same manner as in Synthesis Example 4 except that the Qdot605-aggregated silica nanoparticle synthesized in synthesis Example 3 was used instead of the FITC-aggregated silica nanoparticle.

Production of Biotinylated TXR

Synthesis Example 7

Biotinylated TXR

In THF (dry), 6 mg of TXR (manufactured by DOJINDO LABORATORIES) and 2 mg of ethylenediamine were reacted, and thereafter, by an HPLC (GPC) (manufactured by Japan Analytical Industry Co., Ltd.: LC-9101 (Columns: JAIGEL-1H and JAIGEL-2H, Solvent: THE), purification was carried out. The purified product and amino reactive biotin (manufactured by DOJINDO LABORATORIES) were reacted in THF (dry), and thereafter, by the HPLC (GPC) as described above, purification was carried out in the same manner to obtain a biotinylated TXR.

Production of Anti-Peroxidase Antibody-Binding TXR Silica Nanoparticle Aggregate Synthesis Example 8

Anti-Peroxidase Antibody-Binding TXR Silica Nanoparticle Aggregate

Binding of an anti-peroxidase antibody to the TXR-aggregated silica nanoparticle synthesized in Synthesis Example 2 was carried out according to the following procedure to obtain an anti-peroxidase antibody-binding TXR-aggregated silica nanoparticle.
(Preparation of Fluorescent Aggregate for Antibody Binding)
In PBS containing 2 mM EDTA, the TXR-aggregated silica nanoparticle was dissolved to adjust it up to 3 nM. To this solution, succinimidyl-[(N-maleomidopropionamid)-dodecaethyleneglycol]ester (manufactured by Thermo Scientific, "SM (PEG) 12" (trademark)) was mixed so as to attain a final concentration of 10 mM, and a reaction for 1 hour was carried out. This mixture was centrifuged at 10,000 G for 20 minutes, and the supernatant was removed. Thereafter, PBS containing 2 mM EDTA was added thereto to disperse the precipitate, and centrifugation was carried out again. Further, by the same procedure, washing was carried out 3 times to obtain a fluorescent aggregate for antibody binding.
(Preparation of Reduced Antibody)
To an anti-peroxidase antibody (manufactured by Sigma-Aldrich: P7899), a thiol group-adding treatment was carried out using N-succinimidyl S-acetylthioacetate (SATA), and excessive reaction reagent was removed using a gel filtration column to obtain a reduced antibody solution capable of binding to a silica particle.
(Preparation of Anti-Peroxidase Antibody-Binding Fluorescent Aggregate)
The fluorescent aggregate for antibody binding and the reduced antibody obtained as described above were mixed in PBS containing 2 mM EDTA, and a reaction for 1 hour was carried out. And, 10 mM mercaptoethanol was added thereto to stop the reaction. The obtained solution was centrifuged at 10,000 G for 20 minutes, and the supernatant was removed. Thereafter, PBS containing 2 mM EDTA was added thereto to disperse the precipitate, and centrifugation was carried out again. Further, by the same procedure, washing was carried out 3 times to obtain an anti-peroxidase antibody-binding TXR-aggregated silica nanoparticle.

Production of Avidinylated TXR-Aggregated Silica Nanoparticle

Synthesis Example 9

Binding of streptavidin to the TXR-aggregated silica nanoparticle synthesized in Synthesis Example 2 was carried out according to each of the following procedures to obtain an avidinylated TXR-aggregated silica nanoparticle.
In PBS (phosphate buffered saline) containing 2 mM EDTA (ethylenediaminetetraacetic acid), the TXR-aggregated silica nanoparticle was dissolved to adjust it up to 3 nM. To this solution, SM (PEG) 12 (manufactured by Thermo Scientific, succinimidyl-[(N-maleomidopropionamid)-dodecaethyleneglycol]ester) was mixed so as to attain a final concentration of 10 mM, and a reaction for 1 hour was carried out. This mixture was centrifuged at 10,000 G for 20 minutes, and the supernatant was removed. Thereafter, PBS containing 2 mM EDTA was added thereto to disperse the precipitate, and centrifugation was carried out again. By the same procedure, washing was carried out 3 times to obtain a fluorescent aggregate for streptavidin binding.
On the other hand, to streptavidin, a thiol group-adding treatment was carried out using SATA, and excessive reaction reagent was removed using a gel filtration column to obtain a streptavidin solution capable of binding to a silica particle.
The fluorescent aggregate for binding and the streptavidin obtained as described above were mixed in PBS containing 2 mM EDTA, and a reaction for 1 hour was carried out. And, 10 mM mercaptoethanol was added thereto to stop the reaction. The obtained solution was centrifuged at 10,000 G for 20 minutes, and the supernatant was removed. Thereafter, PBS containing 2 mM EDTA was added thereto to disperse the precipitate, and centrifugation was carried out again. By the same procedure, washing was carried out 3 times to obtain an avidinylated TXR-aggregated silica nanoparticle.

<2. Staining and Observation Step>

Example 1

Effect of Fixation Treatment

On the occasion of carrying out the immunohistochemical staining and the DAB staining for the same tissue section, the effect of the fixation treatment carried out after the color development by DAB is evaluated by the method as described below.

(1) Immunohistochemical Staining

Using the biotinylated TXR-aggregated silica nanoparticle produced in Synthesis Example 5, and a tumor marker kit for examining a tissue, "Ventana I-VIEW PATHWAY HER2 (4B5)" (manufactured by Roche Diagnostics), immunohistochemical staining that is combining fluorescence staining and DAB staining in a human breast tissue (hereinafter referred to as the "fluorescence and DAB double staining") was carried out by the following procedure. The "Ventana I-VIEW PATHWAY HER2 (4B5)" is a kit which contains an anti-HER2 rabbit antibody (4B5), a biotinylated anti-rabbit antibody, and peroxidase-binding avidin as labeled probe biological substances. As a section for staining, a tissue array slide (CB-A712) manufactured by COSMO BIO CO., LTD. was used.

After deparaffinization treatment of the tissue array slide, antigen activation treatment described in the instructions attached to Ventana I-VIEW PATHWAY HER2 (4B5) was carried out. Then, after reaction of the anti-HER2 rabbit antibody (4B5), the biotinylated anti-rabbit antibody, and the peroxidase-binding avidin, a reaction of 0.01 nM biotinylated TXR-aggregated silica nanoparticle for 1 hour was carried out. After washing with PBS, the color development by DAB was carried out using Peroxidase Stain DAB Kit (manufactured by NACALAI TESQUE, INC.: 25985-50).

(2) Fixation Treatment

By immersing the immunohistochemically stained section obtained in the above (1) in a 4% neutral paraformaldehyde aqueous buffer solution for 10 minutes, fixation treatment was carried out.

(3) Dehydration, Clearing, Sealing

The immunohistochemically stained section, on which fixation treatment was carried out in the above (2), was immersed in ethanol to dehydrate it. The dehydrated section was further immersed in xylene, and then dried in the air to perform clearing, and thereby a double stained section was obtained.

(4) Observation

The double stained section obtained in the above (3) was sealed with a slide glass, and, using a general-purpose fluorescent microscope manufactured by Olympus Corporation, BX53, observation was carried out (Fixation Treatment: "Yes"). At the time of measurement, the excitation wavelength was 580 nm, and the measurement wavelength was 630 nm.

As a control, a double stained section obtained by the method in which the fixation treatment in the step (2) in the above-described staining method was not carried out was observed (Fixation Treatment: "No").

As a result of the observation comparison, it was confirmed that carrying out a fixation treatment enables staining that has no decrease in the number of the bright spots of the fluorescence while keeping the DAB stainability (Table 3).

TABLE 3

| Sample | Fixation Treatment | Observation Results |
| --- | --- | --- |
| Fluorescence and DAB Double Staining | Yes | It could be observed that the number of bright spots on cell membrane was the same as in the case where DAB staining is not performed. (The number of the bright spots per cell: 6.1) The DAB stainability was the same as that of the staining method described in the instructions of Ventana I-VIEW PATHWAY HER2 (4B5). |
| Fluorescence and DAB Double Staining | No | It could be observed that the number of bright spots on cell membrane was decreased as compared to that of the case where DAB staining is not performed. (The number of the bright spots per cell: 4.1) The DAB stainability was the same as that of the staining method described in the instructions of Ventana I-VIEW PATHWAY HER2 (4B5). |

Example 2

Comparison with Single Staining Methods

Comparison of the staining in which the reaction of the biotinylated TXR-aggregated silica nanoparticle in the step (1) in the staining method described in Example 1 was not carried out (hereinafter referred to as "DAB single staining"), the staining in which DAB was not added and the color development by DAB was not carried out (hereinafter referred to as "fluorescence single staining"), and the fluorescence and DAB double staining was carried out. The observation was carried out by observation of the morphology and the DAB staining in bright field using a microscope and observation of the bright spots and the brightness of a marker by fluorescence.

As a result of the observation, it was found that, only in the case of the fluorescence and DAB double staining, both of the observation by the bright field and the observation of the bright spots and the brightness of a marker by fluorescence is possible (Table 4).

TABLE 4

|  | Observation of Morphology and DAB Staining in Bright Field | Fluorescence Quantitative Measurement |
| --- | --- | --- |
| DAB Single | o | x |
| Fluorescence Single | x | o |
| Fluorescence and DAB Double Staining | o | o |

Example 3

Comparison of Marker Stainability by Enzyme Reaction Time

When carrying out the color development by DAB using Peroxidase Stain DAB Kit (manufactured by NACALAI TESQUE, INC.: 25985-50) in the staining method described in the instructions attached to Ventana I-VIEW PATHWAY HER2 (4B5) (hereinafter referred to as "the DAB standard staining method"), comparative experiment between the fluorescence and DAB double staining and the DAB single staining for the change in the stainability of a marker (HER2) by changing the enzyme reaction time was carried out.

As a result of the comparative observation, it was found that, in the case of confirming the stainability of the marker using as an indicator the DAB pigmentation property in the bright field observation in these observation methods, by changing the enzyme reaction time from 1 minute to 5 minutes, the DAB pigmentation was increased and the stainability of the marker was heightened; on the other hand, in case of using as an indicator the number of the bright spots and the brightness in the fluorescence and DAB double staining, the marker recognition capability was not changed.

Example 4

Comparison of Staining Methods

Staining by the staining methods described in the below (a) to (d) was carried out, and, for each of them, the pigmentation stainability (bright field observable stainability) compared with the DAB standard staining method, and, the fluorescence stainability compared with the fluorescence single staining were observed and verified using an image analysis software, "ImageJ" (trade name, manufactured by National Institutes of Health). The pigmentation stainability was evaluated by importing the stain images into the image analysis software, converting them to gray scale images, expressing them as gradation values, and evaluating, as an indicator, the shape of the histogram of the gradation values and the percentage of area above a certain threshold in the histogram. The fluorescence stainability was evaluated by measuring the number of the fluorescence signal bright spots with the image analysis software, and evaluating it as an indicator.

If the percentage of area above the threshold in the histogram compared with the DAB single staining is not less than 65%, and the number of the fluorescence signal bright spots per cell compared with the fluorescence single staining is not less than 65%, then it can be considered that information about the expression amount, the localization, and so on of a specific biological substance on the tissue section can be acquired with a high quantitativity and in detail, and thereby the action and the effect of the present invention are exhibited. From the standpoint of the action and the effect as described above, it is preferable that the percentage of area above the threshold in the histogram be is not less than 80%, and the number of the fluorescence signal bright spots per cell be not less than 80%. At the time of measurement, the excitation wavelength was 580 nm, and the measurement wavelength was 630 nm.

(a) Staining that uses the avidinylated TXR-aggregated silica nanoparticle of Synthesis Example 9 instead of the biotinylated TXR-aggregated silica nanoparticle in the staining method described in Example 1 (hereinafter referred to as "peroxidase and TXR-aggregated silica nanoparticle simultaneous staining")

(b) staining in which staining that uses the avidinylated TXR-aggregated silica nanoparticle of Synthesis Example 9 instead of the biotinylated TXR-aggregated silica nanoparticle and the avidinylated peroxidase in the staining method described in Example 1, and DAB staining by a Histofine HER2 kit (MONO) (manufactured by NICHIREI) were simultaneously carried out (hereinafter referred to as "avidinylated phosphor staining+Histofine DAB staining")

(c) Staining that uses the anti-peroxidase antibody-binding TXR-aggregated silica nanoparticle of Synthesis Example 8 instead of the biotinylated TXR-aggregated silica nanoparticle in the staining method described in Example 1 (hereinafter referred to as "fluorescence and DAB double staining that uses an anti-HRP antibody")

(d) Fluorescence and DAB double staining by the staining method described in Example 1

The Histofine HER2 kit (MONO) is a kit which contains a mouse anti-human HER2/neu gene product monoclonal antibody (SV2-61γ) and a peroxidase labeled goat anti-mouse IgG polyclonal antibody (Fab') as labeled biological probe substances. The mouse anti-human HER2/neu gene product monoclonal antibody contained in the kit and the anti-HER2 rabbit antibody used in the fluorescence single staining and the above-described method (b) and contained in "Ventana I-VIEW PATHWAY HER2 (4B5)" are not competed with each other in binding to a human HER2 protein. Therefore, in the "avidinylated phosphor staining+Histofine DAB staining", both staining that allows bright field observation and fluorescence staining are carried out for the same specific biological substance.

As a result, in the peroxidase and TXR-aggregated silica nanoparticle simultaneous staining, the pigmentation stainability compared with the DAB standard staining and the number of the fluorescence signal bright spots per cell compared with the fluorescence single staining were remarkably decreased.

In the avidinylated phosphor staining+Histofine DAB staining, there was no remarkable decrease in the stainability compared with the DAB standard staining and the number of the fluorescence signal bright spots per cell compared with the fluorescence single staining, and a stable stainability was shown.

In the fluorescence and DAB double staining that uses an anti-HRP antibody and in the fluorescence and DAB double staining, more stable stainabilities were shown (Table 5),

TABLE 5

|  | Percentage of Area Above Certain Threshold in Histogram Compared with DAB Standard Staining Method | Number of Fluorescence Signal Bright Spots Per Cell Compared with Fluorescence Single Staining |
|---|---|---|
| (a) Peroxidase and TXR-Aggregated Silica Nanoparticle Simultaneous Staining | 40% | 34% |
| (b) Avidinylated Phosphor Staining + Histofine DAB Staining | 69% | 68% |
| (c) Fluorescence and DAB Double Staining that Uses Anti-HRP Antibody | 82% | 85% |
| (d) Fluorescence and DAB Double Staining | 96% | 98% |

Example 5

Comparison of Composition of Phosphors in Fluorescence and DAB Double Staining

Using the 4 species as described in the below (a) to (d) as labels, the fluorescence and DAB double staining was carried out, and the stainabilities and the bright spot measuring capabilities thereof were compared and considered using a general-purpose fluorescent microscope (manufactured by Olympus Corporation: BX53) and a confocal laser microscope (manufactured by Olympus Corporation: FV1000-D). The excitation wavelength was 400 nm in case of Q-dot605, and 580 nm in case of the biotinylated TXR-aggregated silica nanoparticle; and the measurement wavelength was 630 nm in case of Q-dot605, and 630 nm in case of the biotinylated TXR-aggregated silica nanoparticle. The staining step was carried out in the same manner as in Example 1.

(a) Biotinylated TXR dye (Synthesis Example 7)
(b) Biotinylated Q-dot605 (manufactured by Life Technologies: Q10301 MP)
(c) Biotinylated TXR-aggregated silica nanoparticle (Synthesis Example 5)
(d) Biotinylated Q-dot605-aggregated silica nanoparticle (Synthesis Example 6)

As shown in Table 6 below, in all the cases where these labels were individually used, brightness evaluation could be carried out with the confocal laser microscope. In addition, in the cases where labels other than the biotinylated TXR dye (a) were individually used, bright spot measurement could be also carried out.

Further, it was found that, in the cases where the biotinylated TXR-aggregated silica nanoparticle (c) and the biotinylated Q-dot605-aggregated silica nanoparticle (d), which had been aggregated, were individually used as a label, brightness evaluation and bright spot measurement could be carried out also with a general-purpose microscope.

TABLE 6

| Label | Brightness Evaluation | Bright Spot Measurement (Confocal) | Bright Spot Measurement (General-Purpose Microscope) |
|---|---|---|---|
| Biotinylated TXR dye | ◯ | n.d. | n.d. |
| Biotinylated Q-dot605 | ◯ | ◯ | n.d. |
| Biotinylated TXR-Aggregated Silica Nanoparticle | ◯ | ◯ | ◯ |
| Biotinylated Q-dot605-Aggregated Silica Nanoparticle | ◯ | ◯ | ◯ |

Example 6

Consideration of Wavelength in Fluorescence and DAB Double Staining

Using as labels the biotinylated FITC-aggregated silica nanoparticle (Synthesis Example 1) and the biotinylated TXR-aggregated silica nanoparticle (Synthesis Example 2), the fluorescence and DAB double staining was carried out, and verification of the changes in the stainability compared with the DAB single staining and the number of the fluorescence signal bright spots per cell compared with the fluorescence single staining was carried out. The excitation wavelength was 480 nm in case of the biotinylated FITC-aggregated silica nanoparticle, and 580 nm in case of the biotinylated TXR-aggregated silica nanoparticle; and the measurement wavelength was 530 nm in case of the biotinylated FITC-aggregated silica nanoparticle, and 630 nm in case of the biotinylated TXR-aggregated silica nanoparticle. The staining method was carried out in the same manner as in Example 1, and the evaluation of the stainability was carried out in the same manner as in Example 4.

As shown in Table 7, although a little decrease in the number of the bright spots was observed in the staining that uses the biotinylated FITC-aggregated silica nanoparticle, good fluorescence observation could be performed in either case.

TABLE 7

| Label | Stainability Compared with DAB Standard Staining Method | Number of Fluorescence Signal Bright Spots Per Cell Compared with Fluorescence Single Staining |
|---|---|---|
| Biotinylated FITC-Aggregated Silica Nanoparticle | Same Degree | 91% |
| Biotinylated TXR-Aggregated Silica Nanoparticle | Same Degree | 98% |

DESCRIPTION OF SYMBOLS

10 Specific Biological Substance
20 Probe Biological Substance
21 Antibody That Recognizes Specific Biological Substance and Binds Thereto
23 Antibody That Recognizes Peroxidase and Binds Thereto
30 Label That Allows Bright Field Observation (Pigmentation-Inducing Label)
31 Peroxidase
40 Fluorescent Label 50 Antibody That Recognizes and Binds to Antibody That Recognizes Specific Biological Substance and Binds Thereto
70 Streptavidin
80 Biotin

The invention claimed is:

1. A method for staining a tissue section, comprising:
   treating a tissue section with a biotinylated antibody wherein the biotinylated antibody directly or indirectly binds to a specific biological substance;
   treating the tissue section with an avidinylated or streptavidinylated label for a bright field observation of the specific biological substance, wherein the avidinylated or streptavidinylated label binds to the biotinylated antibody;
   treating the tissue section with a biotinylated fluorescent label for the specific biological substance, wherein the biotinylated fluorescent label binds to the avidinylated or streptavidinylated label; and
   observing a pigmentation of the avidinylated or streptavidinylated label for the bright field observation on the tissue section and quantitatively observing bright spots of the biotinylated fluorescent label with general-purpose fluorescent microscope to identify a localization and an expression amount of the specific biological substance,
   wherein the specific biological substance is a protein,
   wherein the biotinylated fluorescent label comprises particles, and each of the particles comprises fluorescent substances selected from the group consisting of organic fluorescent dyes and semiconductor nanoparticles that have been aggregated to form the particles,
   wherein the fluorescent substances are aggregated such that the fluorescent substance is inside or on the surface of each of the particles,
   wherein an average particle size of the particles is 50 to 200 nm.

2. The method for staining the tissue section according to claim 1, wherein diaminobenzidine is used as a substrate with the avidinylated or streptavddinylated label for the bright field observation, and. the biotinylated fluorescent label has an excitation wavelength of 450 to 700 nm.

3. The method for staining the tissue section accordng to claim 1,
   wherein the biotinylated fluorescent label comprises a core-shell structure particle or a phosphor-containing nanoparticle,
   wherein the core-shell structure particle has a core and a shell on the core, the shell comprising the fluorescent substances immobilized on the core, and
   wherein the phosphor-containing nanoparticle comprises a base material and the fluorescent substances.

4. The method for staining the tissue section according to claim 1, wherein a coefficient of variation of the particle size is 20% or less.

5. The method for staining the tissue section according to claim 1,
   wherein the biotinylated fluorescent label comprises a phosphor-containing nanoparticle, and the phosphor-containing nanoparticle comprises a base material and the fluorescent substances, and
   wherein the base material includes silica.

6. The method for staining the tissue section according to claim 1, further comprising counting the bright spots to identify the amount of the specific biological substance.

* * * * *